United States Patent [19]

Muramoto et al.

[11] 4,292,322
[45] Sep. 29, 1981

[54] METHOD FOR KILLING INSECTS WITH ELECTRO-MECHANICAL ULTRASONIC NEBULIZER

[75] Inventors: Takayoshi Muramoto, Hiroshima; Kunitaka Orita, Yanai, both of Japan

[73] Assignee: Fumakilla Limited, Tokyo, Japan

[21] Appl. No.: 65,173

[22] Filed: Aug. 9, 1979

Related U.S. Application Data

[63] Continuation of Ser. No. 696,825, Jun. 16, 1976, Pat. No. 4,173,651.

[51] Int. Cl.$^3$ .................. A01N 43/36; A01N 37/00; A01N 37/08
[52] U.S. Cl. .................................... 424/274; 424/306
[58] Field of Search ............................... 424/306, 274

[56] References Cited

U.S. PATENT DOCUMENTS

| | | | |
|---|---|---|---|
| 3,636,059 | 1/1972 | Masanao et al. | 424/306 |
| 3,679,667 | 7/1972 | Fanta | 260/240 R |
| 3,709,960 | 1/1973 | Lutz et al. | 424/212 |
| 3,966,959 | 6/1976 | Addor | 424/306 |
| 4,009,281 | 2/1977 | Okuno | 424/306 |
| 4,173,651 | 11/1979 | Muramoto et al. | 424/306 |

OTHER PUBLICATIONS

Kirk–Othmer–Encyclopedia of Chem. Technology (1969), 2nd Rev. Ed.–vol. 18, pp. 634, 636, 643, 651 and 652.

Primary Examiner—Douglas W. Robinson
Attorney, Agent, or Firm—James E. Nilles

[57] ABSTRACT

A novel method for killing insects on plants or in nearby air comprising vaporizing in air an insecticidal agent with an electro-mechanical ultrasonic nebulizer is disclosed.

2 Claims, No Drawings

METHOD FOR KILLING INSECTS WITH ELECTRO-MECHANICAL ULTRASONIC NEBULIZER

The present application is a continuation-in-part of U.S. application Ser. No. 696,825 filed on June 16, 1976 and issued on Nov. 6, 1979 as U.S. Pat. No. 4,173,651 entitled "Method for Killing Insects and/or Fungi with Electro-Mechanical Ultrasonic Nebulizer and Composition for Said Method" to Muramoto et al, the entire contents of which are hereby incorporated as reference.

This invention relates to a novel method for killing insects on plants or in nearby air comprising vaporizing in air an insecticidal agent with an electro-mechanical ultrasonic nebulizer.

The conventional methods for killing insects are, first of all, the spraying through an atomizer of an insecticidal agent in emulsion, oil suspension, or aqueous solution; secondly, release, by heat, of an insecticidal agent in air, as observed in fumigants, mosquito-killing coils or electric mosquito-killing device; and thirdly, the spraying of an aerosol of an insecticidal agent by gas pressure. Of these methods, the spraying by atomizer is not capable of realizing a uniform dispersion of an insecticidal agent over a wide area. To increase the overall effect of the spraying, a large quantity of the agents is needed. For this reason, this method is not economical. The second conventional method releases only a small quantity of an insecticidal agent in a given time, so, application over a relatively long time is needed to do the job. The last method of using an aerosol is generally more expensive than the first two.

Basic investigation of ultrasonic nebulization started rather early, but, it has not been applied to insecticidal agents. In experiments, even on a small scale, only solvent is nebulized when a solution of a high boiling insecticidal agent in a solvent is subjected to ultrasonic nebulization, and the high boiling insecticidal agent remains in the mother liquor, and ultimately the mother liquor consists only of the high boiling material thereby completely preventing the nebulization.

In order to eliminate these drawbacks of the prior art, the inventors of the present invention investigated to make possible the practice of ultrasonic nebulization of insecticidal agents, and found that selection of particular frequency, solvent and content of insecticidal ingredient leads to success in ultrasonic nebulization of the insecticidal ingredient, and additional selection of the size of particles to be released enables putting the technique to practical use. On the basis of these facts, the present invention was completed.

Therefore, the principal object of this invention is to provide a novel method for killing insects which has overcome the above mentioned defects of the conventional methods. The detailed description of this invention will be carried in the following passages.

This invention relates to a novel method for killing insects on plants or in nearby air characterized by vaporizing in air an insecticidal agent atomized with an electro-mechanical ultrasonic nebulizer, and an insecticidal composition to be employed in this method.

The electro-mechanical ultrasonic nebulizer to be employed in the method of this invention is such that the number of vibrations is 800,000–1,700,000 Hz, and the outlet-power may be about 10–40 W.

A suitable particle size of the above mentioned insecticidal agents when they are released into air can be selected by varying the number of vibrations of the ultrasonic nebulizer. The co-relationship between the particle size and the number of the vibrations is illustrated in the following tables.

TABLE I

| (on oil base) | |
|---|---|
| Number of Vibrations (MHz) | Average Particle Size ($\mu$) |
| 0.8 | 4.3 |
| 1.0 | 3.7 |
| 1.2 | 3.3 |
| 1.4 | 2.9 |
| 1.6 | 2.6 |
| 1.8 | 2.3 |
| 2.0 | 2.0 |

Atomization is also made possible at low temperature with the nebulizer. If the released particle size is as small as 0.5 to 5 microns, the insecticidal agent can be uniformly dispersed with great ease. More than that, since the agent is easily inhaled as poison by noxious insects, it has only to be used in a small quantity to exhibit its effect. In addition, vaporization at low temperatures will eliminate the loss of the active ingredient from the agent. Another advantage of our method is apparent when it is employed in agricultural or horticultural buildings such as greenhouse or vinyl plastic hothouse. Manual labor that accompanies the conventional method of application, for example, by spraying or evaporation, is entirely unnecessary for our insecticidal method, and therefore, not only is a saving of labor achieved but the health of workers is ensured. In addition, the temperature and moisture in the insulated agricultural or horticultural buildings are so high that plants in them are easily infested with harmful insects. However, according to the method of our invention, because the agent is atomized and vaporized at high concentrations, its application will not result in the increase of humidity. What is more, uniform dispersion of the agent is possible within a short period, covering the wide space of a greenhouse, for example.

The insecticidal compositions to be employed in the electro-mechanical ultrasonic nebulizer of the present invention are as follows:

a solution of allethrin in n-tridecane;
a solution of resmethrin in n-tridecane;
a solution of phenothrin in n-tridecane;
a solution of phthalthrin in n-tridecane;
a solution of permethrin in n-tridecane;
a solution of allethrin in n-tetradecane;
a solution of resmethrin in n-tetradecane;
a solution of phenothrin in n-tetradecane;
a solution of phthalthrin in n-tetradecane;
a solution of permethrin in n-tetradecane;
a solution of allethrin in kerosene-isopropyl alcohol;
a solution of resmethrin in kerosene-isopropyl alcohol;
a solution of phenothrin in kerosene-isopropyl alcohol;
a solution of phthalthrin in kerosene-isopropyl alcohol;
a solution of permethrin in kerosene-isopropyl alcohol;
a solution of kadethrin in kerosene-isopropyl alcohol;
a solution of cypermethrin in kerosene-isopropyl alcohol;
a solution of decamethrin in kerosene-isopropyl alcohol;

a solution of permethrin-allethrin in kerosene-isopropyl alcohol;

a solution of phenothrin-allethrin in kerosene-isopropyl alcohol;

a solution of kadethrin-allethrin in kerosene-isopropyl alcohol;

a solution of decamethrin-allethrin in kerosene-isopropyl alcohol;

a solution of cypermethrin-allethrin in kerosene-isopropyl alcohol;

a solution of permethrin-phthalthrin in kerosene-isopropyl alcohol;

a solution of phenothrin-phthalthrin in kerosene-isopropyl alcohol;

a solution of kadethrin-phthalthrin in kerosene-isopropyl alcohol;

a solution of decamethrin-phthalthrin in kerosene-isopropyl alcohol;

a solution of cypermethrin-phthalthrin in kerosene-isopropyl alcohol;

a solution of permethrin in kerosene-ethyl alcohol;

a solution of permethrin in kerosene-ethyl malonate;

a solution of permethrin in kerosene-sesame oil;

a solution of permethrin in kerosene-sesame oil-isopropyl alcohol; and a solution of permethrin in kerosene-isopropyl alcohol-ethyl alcohol.

According to the inventors' research, atomization with the nebulizer is influenced by the concentration of the insecticidal component, the solvent used, the ultrasonic frequency used and the size of the particles nebulized.

The concentration of the insecticidal and/or fungicidal composition mentioned above may not exceed 25% by weight. A concentration greater than this level is not applicable on an industrial scale because too much decomposition of the active ingredient takes place. The effective concentration ranges preferably from 2 to 20% by weight. In contrast with the conventional method of using an oil suspension, our method allows an effective application of a small quantity of the insecticidal composition at high concentrations, and therefore, contamination of the active ingredient by the solvent is at minimum and an extremely economical operation of the method is realized. The insecticidal composition thus prepared is atomized with an electro-mechanical ultrasonic nebulizer having a frequency within the range of from 800,000 to 1,700,000 Hz.

This invention will be more specifically explained by the following working examples and experimental data.

EXAMPLE 1

A solution of each of allethrin, resmethrin, phenothrin, phthalthrin and permethrin in n-tridecane at a concentration of 5 w/v % was prepared. These solutions were subjected to an ultrasonic frequency of 1,050,000 Hz (Power: 20 W) to atomize the insecticidal solutions in a room of 20 mats (a mat is 18 square feet) in which ten dishes each containing 10 cockroaches (Blattella germanica) (female adult) were equally spaced. Thus, the insecticidal efficacy was determined.

TABLE 1

Insecticidal efficacy of n-tridecane solutions (in room of 20 mats)

| | Quantity of agent and insecticidal efficacy | | | | |
|---|---|---|---|---|---|
| | Quantity of agent | Knock down (%) after | | | Kill (%) after |
| Name of agent | atomized (g) | 15 min | 30 min | 60 min | 1 day |
| Allethrin | 2.02 | 88 | 100 | 100 | 100 |
| Resmethrin | 1.80 | 77 | 98 | 100 | 100 |
| Phenothrin | 1.66 | 80 | 100 | 100 | 100 |
| Phthalthrin | 1.82 | 80 | 98 | 100 | 100 |
| Permethrin | 1.52 | 84 | 100 | 100 | 100 |

EXAMPLE 2

Under the same conditions as in Example 1, the insecticidal efficacy of the following n-tetradecane solutions was determined.

TABLE 2

Insecticidal efficacy of n-tetradecane solutions (in room of 20 mats)

| | Quantity of agent and insecticidal efficacy | | | | |
|---|---|---|---|---|---|
| | Quantity of agent | Knock down (%) after | | | Kill (%) after |
| Name of agent | atomized (g) | 15 min | 30 min | 60 min | 1 day |
| Allethrin | 1.97 | 90 | 100 | 100 | 100 |
| Resmethrin | 1.62 | 85 | 100 | 100 | 100 |
| Phenothrin | 1.56 | 80 | 100 | 100 | 100 |
| Phthalthrin | 1.53 | 90 | 100 | 100 | 100 |
| Permethrin | 1.41 | 77 | 100 | 100 | 100 |

EXAMPLE 3

Five insecticides, allethrin, resmethrin, phenothrin, phthalthrin and permethrin, were dissolved in kerosene-isopropyl alcohol (78:7 by weight) as a concentration of 15 w/v %, respectively. These solutions were subjected to an ultrasonic frequency of 1,150,000 Hz (Power: 20 W) to atomize the insecticidal solutions in a room of 6 mats in which 5 dishes each containing 10 cockroaches (Blattella germanica) (female adult) were equally spaced. Thus, the insecticidal efficacy was determined.

TABLE 3

Insecticidal efficacy of kerosene-isopropyl alcohol solutions (in room of 6 mats)

| | Quantity of agent and insecticidal efficacy | | | | | | |
|---|---|---|---|---|---|---|---|
| | Quantity of agent | Knock down (%) after | | | | | Kill (%) after |
| Name of agent | atomized (mg) | 5 min | 10 min | 15 min | 20 min | 30 min | 60 min | 1 day |
| Allethrin | 400 | 18 | 32 | 68 | 76 | 84 | 96 | 100 |
| Resmethrin | 400 | 20 | 38 | 80 | 94 | 100 | 100 | 100 |
| Phenothrin | 400 | 18 | 36 | 58 | 78 | 87 | 100 | 100 |
| Phthalthrin | 400 | 16 | 20 | 61 | 78 | 88 | 98 | 100 |

TABLE 3-continued

Insecticidal efficacy of kerosene-isopropyl alcohol solutions (in room of 6 mats)

| Name of agent | Quantity of agent atomized (mg) | Knock down (%) after | | | | | | Kill (%) after 1 day |
|---|---|---|---|---|---|---|---|---|
| | | 5 min | 10 min | 15 min | 20 min | 30 min | 60 min | |
| Permethrin | 400 | 20 | 48 | 70 | 86 | 94 | 100 | 100 |

EXAMPLE 4

Three insecticides, kadethrin, cypermethrin and decamethrin (each, 50% solution in N,N-dimethylformamide) were dissolved in kerosene-isopropyl alcohol (85:5 by weight) at an insecticide concentration of 5% (w/v), respectively. These solutions were subjected to an ultrasonic frequency of 1,050,000 Hz (Power: 20 W) to atomize the insecticidal solutions in a room of 20 mats in which 10 dishes each containing 10 cockroaches (Blattella germanica) (female adult) were equally spaced. Thus, the insecticidal efficacy was determined.

TABLE 4

Insecticidal efficacy of kerosene-isopropyl alcohol solutions (in room of 20 mats).

| Name of agent | Quantity of agent atomized (g) | Knock down (%) after | | | Kill (%) after 1 day |
|---|---|---|---|---|---|
| | | 15 min | 30 min | 60 min | |
| Kadethrin | 1.33 | 72 | 98 | 100 | 100 |
| Cypermethrin | 1.28 | 76 | 100 | 100 | 100 |
| Decamethrin | 1.37 | 78 | 100 | 100 | 100 |

EXAMPLE 5

Each of five insecticides, permethrin, phenothrin, kadethrin, decamethrin and cypermethrin (each, 50% solution in N,N-dimethylformamide), was mixed with either allethrin or phthalthrin in an insecticide weight ratio of 5:1, and was dissolved in kerosene-isopropyl alcohol (90:10 by weight) at a concentration of 5% (w/v). The resulting solutions were subjected to an ultrasonic frequency of 1,050,000 Hz (Power: 20 W) to atomize the insecticidal solutions in a room of 6 mats in which 5 dishes each containing 10 cockroaches (*Blattella germanica*) (female adult) were equally spaced. Thus, the insecticidal efficacy was determined.

TABLE 5

Insecticidal efficacy of mixed agents in kerosene-isopropyl alcohol (in room of 6 mats)

| Name of agent | Quantity of agent atomized (mg) | Knock down (%) after | | | | | | Kill (%) after 1 day |
|---|---|---|---|---|---|---|---|---|
| | | 5 min | 10 min | 15 min | 20 min | 30 min | 60 min | |
| Permethrin + allethrin | 230 45 | 26 | 40 | 52 | 60 | 78 | 100 | 100 |
| Phenothrin + Allethrin | 234 47 | 24 | 38 | 46 | 52 | 64 | 100 | 100 |
| Kadethrin + Allethrin | 236 47 | 20 | 38 | 44 | 52 | 62 | 100 | 100 |
| Decamethrin + Allethrin | 243 49 | 28 | 43 | 56 | 68 | 80 | 100 | 100 |
| Cypermethrin + Allethrin | 239 48 | 26 | 40 | 54 | 64 | 80 | 100 | 100 |
| Permethrin + Phthalthrin | 221 44 | 18 | 28 | 36 | 46 | 66 | 100 | 100 |
| Phenothrin + Phthalthrin | 226 45 | 16 | 26 | 32 | 42 | 64 | 100 | 100 |
| Kadethrin + Phthalthrin | 232 46 | 13 | 22 | 30 | 38 | 60 | 92 | 100 |
| Decamethrin + Phthalthrin | 237 47 | 20 | 34 | 49 | 60 | 72 | 100 | 100 |
| Cypermethrin + Phthalthrin | 230 45 | 18 | 28 | 40 | 52 | 68 | 100 | 100 |

EXAMPLE 6

To a 10% (w/v) permethrin solution in kerosene, there was added one of ethyl alcohol, sesame oil, ethyl malonate, isopropyl alcohol-ethyl alcohol (1:1 by weight) and isopropyl alcohol-sesame oil (1:1 by weight) in a proportion of 7% by weight. Each of the prepared solutions were subjected to an ultrasonic frequency of 1,050,000 Hz (Power: 20 W) to atomize the insecticidal solution in a room of 6 mats in which 5 dishes each containing 10 cockroaches (*Blattella germanica*) (female adult) were equally spaced. Thus, the insecticidal efficacy was determined.

TABLE 6

Insecticidal efficacy of mixed solvent solutions (in room of 6 mats)

| Name of solvent | Quantity of agent atomized (mg) | Knock down (%) after | | | | | | Kill (%) after 1 day |
|---|---|---|---|---|---|---|---|---|
| | | 5 min | 10 min | 15 min | 20 min | 30 min | 60 min | |
| Isopropyl alcohol | 400 | 20 | 48 | 70 | 86 | 94 | 100 | 100 |
| Ethyl alcohol | 405 | 20 | 46 | 70 | 84 | 92 | 100 | 100 |
| Sesame oil | 402 | 18 | 46 | 67 | 83 | 90 | 100 | 100 |
| Ethyl malonate | 400 | 16 | 40 | 64 | 78 | 88 | 100 | 100 |
| Isopropyl alcohol + Sesame oil | 400 | 24 | 50 | 70 | 88 | 96 | 100 | 100 |
| Isopropyl alcohol + Ethyl alcohol | 400 | 22 | 48 | 72 | 84 | 90 | 100 | 100 |

Note:
Kill of cockroaches (*periplaneta fulliginosa*) was increased only with addition of sesame oil.

What is claimed is:

1. A method of killing insects on plants or in nearby air comprising the steps of:
applying thereto an insecticidal effective amount of a composition selected from the group consisting of the following solutions, and wherein each solution contains an agent and a solvent, said agent being about 2 to 20% by weight of said composition:
a solution of allethrin in n-tridecane;
a solution of resmethrin in n-tridecane;
a solution of phenothrin in n-tridecane;
a solution of phthalthrin in n-tridecane;
a solution of permethrin in n-tridecane;
a solution of allethrin in n-tetradecane;
a solution of resmethrin in n-tetradecane;
a solution of phenothrin in n-tetradecane;
a solution of phthalthrin in n-tetradecane;
a solution of permethrin in n-tetradecane;
a solution of allethrin in kerosene-isopropyl alcohol (78:7 by weight);
a solution of resmethrin in kerosene-isopropyl alcohol (78:7 by weight);
a solution of phenothrin in kerosene-isopropyl alcohol (78:7 by weight);
a solution of phthalthrin in kerosene-isopropyl alcohol (78:7 by weight);
a solution of permethrin in kerosene-isopropyl alcohol (85:5 by weight);
a solution of kadethrin in kerosene-isopropyl alcohol (85:5 by weight);
a solution of cypermethrin in kerosene-isopropyl alcohol (85:5 by weight);
a solution of decamethrin in kerosene-isopropyl alcohol (85:5 by weight);
a solution of permethrin-allethrin in kerosene-isopropyl alcohol (90:10 by weight);
a solution of phenothrin-allethrin in kerosene-isopropyl alcohol (90:10 by weight);
a solution of kadethrin-allethrin in kerosene-isopropyl alcohol (90:10 by weight);
a solution of decamethrin-allethrin in kerosene-isopropyl alcohol (90:10 by weight);
a solution of cypermethrin-allethrin in kerosene-isopropyl alcohol (90:10 by weight);
a solution of permethrin-phthalthrin in kerosene-isopropyl alcohol (90:10 by weight);
a solution of phenothrin-phthalthrin in kerosene-isopropyl alcohol (90:10 by weight);
a solution of kadethrin-phthalthrin in kerosene-isopropyl alcohol (90:10 by weight);
a solution of decamethrin-phthalthrin in kerosene-isopropyl alcohol (90:10 by weight);
a solution of cypermethrin-phthalthrin in kerosene-isopropyl alcohol (90:10 by weight);
a solution of permethrin in kerosene-ethyl alcohol (93:7 by weight);
a solution of permethrin in kerosene-ethyl malonate (93:7 by weight);
a solution of permethrin in kerosene-sesame oil (93:7 by weight);
a solution of permethrin in kerosene-sesame oil-isopropyl alcohol (93% kerosene and equal mixtures of the other two solvents); and
a solution of permethrin in kerosene-isopropyl alcohol-ethyl alcohol (93% kerosene and equal mixtures of the other two solvents),
wherein said composition is applied by nebulization in an electromechanical ultrasonic transducer operating in a frequency range of between 800,000 and 1,700,000 Hz to effect atomization and vaporization in air of a uniform concentration of said composition, the atomized and vaporized particles of said composition having a particle size in the range of 0.5 to 5 microns.

2. A method of killing insects according to claim 1 wherein each of the insecticide agents permethrin, phenothrin, kadethrin, decamethrin and cypermethrin (each, 50% solution in N,N-dimethylformamide) are mixed with either allethrin or phthalthrin, in a weight ratio of 5:1, and are dissolved in kerosene-isopropyl alcohol (90:10 by weight) at a concentration of 5% (w/v).

* * * * *